United States Patent [19]

Akin et al.

[11] Patent Number: 4,472,439

[45] Date of Patent: Sep. 18, 1984

[54] HEAT TREATMENT FOR LIVE YEAST CELL PASTES

[75] Inventors: Cavit Akin, Naperville, Ill.; John A. Ridgway, LaPorte, Ind.

[73] Assignee: Standard Oil Company (Indiana), Chicago, Ill.

[21] Appl. No.: 110,208

[22] Filed: Jan. 7, 1980

Related U.S. Application Data

[63] Continuation-in-part of Ser. No. 890,580, Mar. 20, 1978, abandoned.

[51] Int. Cl.³ .................................................. A23L 1/28
[52] U.S. Cl. ..................................... 426/62; 435/255; 435/256; 435/260
[58] Field of Search .................. 426/62; 435/255, 256, 435/260

[56] References Cited

U.S. PATENT DOCUMENTS

| | | | |
|---|---|---|---|
| 3,150,061 | 9/1964 | Dalby et al. | 426/62 |
| 3,295,990 | 1/1967 | Ferrara et al. | 435/256 X |
| 3,427,223 | 2/1969 | Frankenfield et al. | 435/248 |
| 3,844,893 | 10/1974 | Hitzman | 435/247 |
| 3,865,691 | 2/1975 | Ridgeway et al. | 435/247 |
| 3,885,050 | 5/1975 | Rideway et al. | 435/255 X |
| 4,192,897 | 3/1980 | Kajinami et al. | 426/62 X |

FOREIGN PATENT DOCUMENTS 1266503  3/1972  United Kingdom ................ 435/260

*Primary Examiner*—Joseph M. Golian
*Attorney, Agent, or Firm*—Marjorie D. Hunter; William T. McClain; William H. Magidson

[57] ABSTRACT

A heat treatment for live yeast cell slurries and pastes, which comprises heating the slurry or paste at a temperature of about 60° C. or greater for a sufficient period of time, increases the fluidity of the slurry or paste and allows more highly concentrated suspensions to be processed than otherwise possible.

6 Claims, No Drawings

HEAT TREATMENT FOR LIVE YEAST CELL PASTES

This application is a continuation-in-part of copending application Serial No. 890,580 filed Mar. 20, 1978, now abandoned.

FIELD OF THE INVENTION

This invention relates to yeast fermentation processes and methods for treating yeast materials. More particularly, it relates to methods of increasing the fluidity and handling properties of yeast slurries and pastes to facilitate processing of more highly concentrated materials.

DESCRIPTION OF THE PRIOR ART

Processes for making yeast, to which the method of this invention is applicable, are well known in the art. One such process is disclosed in U.S. Pat. No. 3,865,691 to Ridgway et al., wherein a yeast such as *Candida utilis* is grown aseptically on an ethanol substrate under oxygen-limited conditions. The fermentation is carried out continuously in a fermentor into which micro- and macro-nutrients are added as needed. The resulting fermentor broth contains a concentration of yeast cells typically ranging from about 0.5 to 5 weight percent. The broth is passed through a separator such as a centrifuge to concentrate the broth into a slurry, commonly referred to as the yeast cream. The yeast cream typically contains about 15–17 weight percent yeast cells, although it may go as high as 20 weight percent. The yeast cream is then directed to a spray dryer to yield the final product.

It is known that easily flowing slurries are handled better in spray dryers preferred for such a process. In the past it has been necessary to maintain the material leaving the separator at a sufficiently low cell concentration (less than 20 weight percent) to keep the stream flowable for easy handling and effective dryer operation, even though a large amount of water still must be removed to dry the product. The viscosity of these yeast suspensions increases exponentially with concentration. Slurries having a cell concentration between 9 and 16 weight percent are handled most easily (having viscosities between 1 and 500 centipoise (cp.), whereas those materials having a more paste-like consistency with a cell concentration greater than 21 weight percent (245,000 cp.) will not readily flow and heretofore have not been able to be processed and dried in current equipment. It would be very desirable to be able to process and spray dry those materials having the higher cell concentrations, but thus far the attendant increase in viscosity has made such a process impossible to achieve. Simple centrifugation can produce yeast pastes having a cell concentration of about 21–30 weight percent, and still more concentrated materials can be produced by additional filtration, but the viscosities of such materials are prohibitive. For example, yeast suspensions of *Candida utilis* yeast having a concentration of about 20 weight percent have a corresponding viscosity of about 47,500 cp., whereas concentrations of about 30 weight percent have viscosities of over 8,000,000 cp. (beyond the measurable limits of available equipment). These numbers depend to some extent upon the type of yeast used, but are believed to be representative of many yeasts. If yeast materials having such higher concentrations could be made more fluid, a processing advantage could be realized in that the attainment of higher concentrations would require the removal of less water by the dryers and could also reduce the amount of intercellular salt retained in the dried product, the salt being present in the water to be removed. Also, in terms of energy, dewatering of slurries or pastes is accomplished more efficiently by centrifugation or film evaporation than by spray drying.

Therefore, it is an object of this invention to increase the fluidity of yeast cell slurries and pastes to permit processability of more concentrated materials in conventional spray dryers.

This and other objects of this invention will become apparent upon further reading of this specification.

SUMMARY OF THE INVENTION

It has been discovered that live yeast cell suspensions, including suspensions variously referred to as slurries, pastes, and cakes, strangely behave similarly to melting solids when exposed to a heat treatment according to this invention. After such a treatment these materials are made more fluid and attain flow characteristics resembling those of a less concentrated material. Such a treatment permits easier handling and processability of otherwise difficult or impossible materials and also facilitates greater salt removal from the yeast product, due to the presence of less of the fermentor broth in the yeast material after it has been concentrated. It also provides for water removal in a more energy efficient manner.

Conveniently, an effective heat treatment for this purpose can generally be achieved by pasteurization, which is generally carried out at about 80° C. for about 1½ minutes or so. Although such conditions have been used to pasteurize yeast slurries containing 15–17 weight percent cells for several years, until Applicants' discovery no one has realized the effect such a treatment has on yeast slurries and consequently no one has been able to take advantage of this phenomenon. The benefits of this discovery cannot be appreciated until it is applied to relatively non-flowing yeast compositions which have a yeast concentration of at least 21 weight percent.

In one aspect, the invention resides in an improved process for making yeast comprising the steps of withdrawing live yeast cells from a fermentor as an aqueous broth containing from about 0.5 to about 5 weight percent yeast, partially dewatering the broth to a more concentrated yeast suspension, and drying the yeast suspension, wherein the improvement comprises combining a heat treatment step with at least one concentrating step such that a final yeast suspension having a concentration of 21 weight percent or greater is produced having a consistency equivalent to a yeast suspension having a concentration of about 20 weight percent or less, said heat treatment comprising heating a yeast suspension at a temperature of about 60° C. or greater for a time sufficient to convert the suspension to a more fluid consistency.

In another aspect, the invention resides in an improved process for making yeast wherein live yeast cells are withdrawn from a fermentor as a broth containing from about 0.5 to about 5 weight percent yeast, the improvement comprising concentrating the live yeast broth to a material containing a yeast cell concentration of 21 weight percent or greater, but preferably not more than about 33 weight percent, and heating the paste or cake to a temperature of about 60° C. or greater for a time sufficient to convert the material to a more fluid consistency. Time sufficient to accomplish this result will be readily determined by one skilled in the art by observation without undue experimentation. Generally, however, the time required to achieve this conversion in consistency will be from about 1 minute to up to about 4 hours, preferably not longer than 30 minutes, and most likely from about 1 to about 10 minutes. The length of time will depend largely on the temperature used, with the higher temperatures requiring the shorter treatment times. Preferred treatment temperatures range between 65° C. and 85° C. with a corresponding treatment time in the range of about 1 to 10 minutes. Temperatures above 100° C. are less desirable due to possible adverse effects on product quality due to the sensitive nature of the yeast composition. The thus-treated material can then be subsequently dried to yield a final product, or it can be further concentrated, as by centrifugation or filtration, before being dried. In such a case the resulting supernatant can be recycled back to the fermentor.

In still another aspect, the invention resides in a process for making yeast wherein live yeast is withdrawn from a fermentor as a broth containing from about 0.5 to about 5 weight percent yeast and concentrated to a slurry-like consistency having a cell concentration of from about 15 to about 20 weight percent, the improvement comprising heating the slurry to a temperature of about 60° C. or greater for a time sufficient to convert the slurry to a more fluid consistency and partially dewatering the heat-treated slurry to a cell concentration of 21 weight percent or greater, and preferably from 21 to about 26 weight percent. The time and temperature ranges previously set forth above are also applicable to this embodiment.

In each case, however, the heat treatment permits removal of about 25 to 35 percent of the water in the original suspension by a method which is more energyefficient than spray drying. Another advantage obtained by treating these yeast materials according to this invention is that charging a higher cell concentration to the spray dryer yields an increase in product particle size, which in turn results in lower product stack emissions.

The preferred yeast is *Candida utilis*.

DESCRIPTION OF THE PREFERRED EMBODIMENTS

In one preferred mode of operation *Candida utilis* yeast is produced in an ethanol, water, and minerals medium in a continuous fermentor and withdrawn as a broth containing from 0.5 to 5 weight percent yeast cells. The broth is concentrated by centrifugation to a paste containing a cell concentration of from about 20 to about 26 weight percent. The paste is preferably heated to from about 65° C. to about 85° C. for from about 1 to about 10 minutes to yield a more easily flowing cell material which has a consistency or viscosity equivalent to a slurry having a concentration of 20 weight percent or less. This material is directed to a spray dryer which produces the final product or, alternatively, the heat-treated material can be centrifuged to remove more liquid as a supernatant which can be recycled to the fermentor. The centrifugate is then dried.

In the most preferable mode of operation this procedure can be varied slightly by using standard centrifugal equipment to first concentrate the broth to obtain the typical 15-20 weight percent slurry. This slurry is then heated to from about 65° C. to about 85° C. for from about 1 minute to about 10 minutes to increase the fluidity of the slurry, which is then partially dewatered by thin film evaporation to a concentration of from about 21 to about 26 weight percent. The resulting yeast material has flow characteristics equivalent to a slurry having a concentration of 20 weight percent or less and similar to the starting slurry and can be completely dewatered by spray drying. Partial dewatering by evaporation is preferable to centrifugation because the heat treatment solubilizes a portion of the cells and evaporation avoids what otherwise might be excessive product losses.

The following examples serve to illustrate the basis for this invention.

EXAMPLE 1

*Candida utilis* yeast (ATCC 9256) was grown in a continuous fermentor in an aqueous ethanol and minerals medium. The cell suspension was stored overnight at about 3° C. and centrifuged to obtain a cell paste containing about 25% dry weight and having a viscosity of more than 8,000,000 cp.

The cell paste was then placed in a test tube and heated in a boiling water bath. The temperature of the paste gradually increased from about 23° C. to about 68° C., at which point the paste structure had collapsed to form a more fluid consistency. The collapse of the yeast paste visually appeared to occur between about 60° C., and 68° C. This phenomenon closely resembled the melting of solids.

EXAMPLE 2

Ten grams of Torula yeast (*Candida utilis*) paste as produced in Example 1 was placed in a test tube and heated for 20 minutes in a 70° C. water bath to obtain an easily flowing, slurry-like material having a viscosity of about 1,000 cp. When the material was cooled back to room temperature it retained its slurry-like flow characteristics. It did not revert back to the paste form.

EXAMPLE 3

The slurry-like material obtained according to the heat treatment described in Example 2 was centrifuged to yield a material having a more paste-like consistency having a dry weight of about 32.6% and a viscosity of more than 8,000,000 cp. Centrifugation yielded about 36 weight percent of liquid as a light brown-colored supernatant having a dry weight of about 5.7%.

EXAMPLE 4

The paste-like material obtained by the centrifugation of the slurry of the Example 3 was reheated in the 70° C. bath. The consistency did not appear to change. The ash content of the final material was 6% (reduced from 8% in the original paste obtained in Example 1) as a result of the centrifugation step in Example 3.

EXAMPLE 5

*Candida utilis* yeast was grown in a continuous fermentor in an aqueous ethanol and minerals medium. The resulting yeast broth was concentrated by centrifugation to a yeast cream having a solids concentration of about 15 weight percent (viscosity of about 500 cp.), which was pasteurized (heat treated) at about 80° C. for about 1½ minutes to yield a more fluid slurry. The heat-treated yeast cream was then concentrated to about 25 weight percent solids by evaporation in a single effect evaporator consisting of a plate and frame type steam heater and a centrifugal vapor-liquid separator. The concentrated yeast material had a viscosity of about 6,600 cp., which is well below the viscosity of a typical 20 weight percent slurry (47,500 cp.) and very fluid. This concentrated material was then spray dried and evaluated for product quality, which was not significantly effected by the additional evaporation step used in this process.

EXAMPLE 6

To determine whether this phenomenon occurs with other yeasts, about 450 grams of a *Saccharomyces cerevisiae* yeast paste having a dry weight of about 29 percent and a viscosity of greater than 8,000,000 cp. was heated in a boiling water bath for 20 minutes and observed as the paste temperature increased. The paste started to "melt" at about 60° C. and was completely collapsed at 68° C., indicating that this phenomenon is not peculiar to *Candida utilis* alone. The final viscosity of the melted paste was about 58,500 cp.

From reading the teachings of this specification it will be apparent to those skilled in the art that many variations from these examples, shown for purposes of illustration, can be made without departing from the scope of this invention.

We claim:

1. In a process for making yeast wherein live yeast is withdrawn from a fermentor as a broth containing from about 0.5 to about 5 weight percent yeast, the improvement comprising concentrating the live yeast broth to a paste containing a yeast cell concentration of from 21 weight percent or greater and heating the paste to a temperature of from about 65° C. to about 85° C. for a time sufficient to convert the paste to a more fluid consistency equivalent to that of a yeast suspension having a concentration of about 20 weight percent or less.

2. The process of claim 1 wherein the paste is heated at from about 65° C. to about 85° C. for from about 1 to about 10 minutes.

3. The process of claim 1 wherein the paste is heated to about 68° C.

4. The process of claim 1 wherein the heat-treated yeast material is dried.

5. The process of claim 1 wherein the heat-treated yeast material is further concentrated by centrifugation and dried.

6. The process of claim 1 wherein the yeast is *Candida utilis*.

* * * * *